Oct. 24, 1950 H. C. SWIM Plant Pat. 985
ROSE PLANT
Filed Dec. 6, 1949
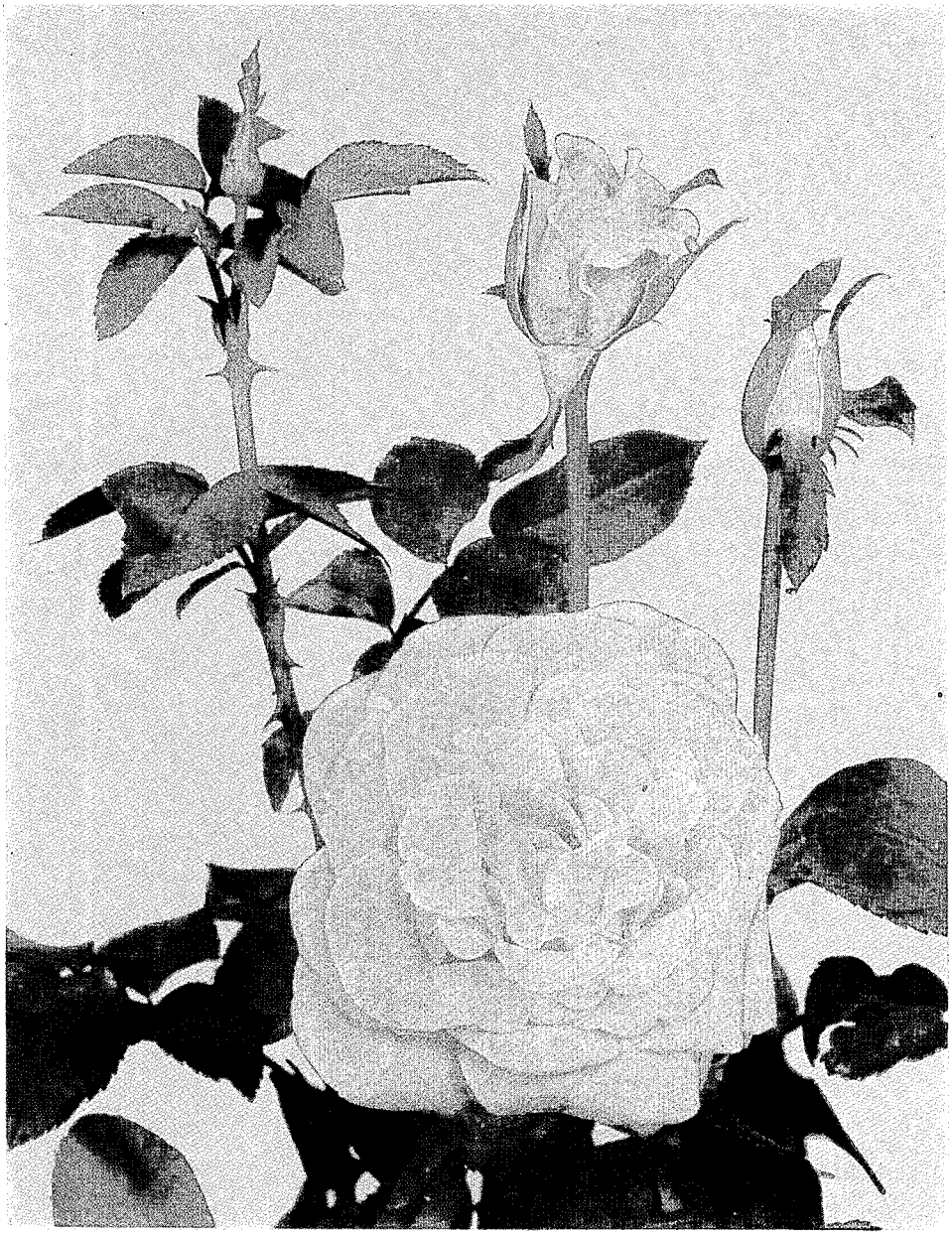
Inventor
H. C. Swim
By: Robert Cobb
Attorneys Patented Oct. 24, 1950

Plant Pat. 985

UNITED STATES PATENT OFFICE

985

ROSE PLANT

Herbert C. Swim, Ontario, Calif., assignor to Armstrong Nurseries, Inc., Ontario, Calif., a corporation of California Application December 6, 1949, Serial No. 131,289

1 Claim. (Cl. 47—61)

The present invention relates to a new and distinct variety of rose plant, resulting from crossing "Charlotte Armstrong" and an unnamed seedling, with the object of producing an improved rose variety by combining as many of the desirable characteristics of the parent varieties as possible.

This new variety is characterized as to novelty by the following combination of distinctive features:

(1) A flower with a bright, unfading type of red, as more specifically described and illustrated herein, with a heavy texture or substantial substance of petal that is to be found in very few roses, particularly in the red shade, such substance making the variety resistant to injury by sun, heat, rain, etc.; and with a regularity of both bud and flower form, exceptional in roses, but more frequently found in the broad petaled, formal double type of camellia. These qualities give the flower a long lasting quality on either the bush or in the cut flower.

(2) Foliage with an unusual color, both in the young growth and in the mature leaves. The color of the young leaves is particularly striking, being a brighter color of red than in any variety heretofore observed. This reddish coloring is not observable in the mature leaves, but is replaced by an unusual and attractive dark green color. These colors, combined with the abundance in which the leaves are produced, go to make an attractive plant, particularly when considered in connection with its bushy habit of growth.

This new variety is distinct from its pollen parent in the following respects:

(*a*) The pollen parent of this new variety has 18 to 22 petals in the bloom, whereas this new variety has 25 to 40 petals, plus 10 to 20 petaloids.

(*b*) The pollen parent is characterized by a spreading habit, whereas this new variety is typically upright in habit.

(*c*) The mature leaves of the pollen parent are flat, whereas this new variety is characterized by mature leaves with margins rolled downward.

(*d*) This new variety has a flower resistant to weather changes while the flower of the pollen parent is subject to injury by weather changes.

This new variety is distinct from its seed parent, "Charlotte Armstrong," Plant Patent No. 455, as follows:

(1) Whereas the flower of "Charlotte Armstrong" varies from Spectrum Red to Cerise, this new variety varies from Currant Red to Blood Red, a much deeper shade.

(2) The flowers of "Charlotte Armstrong" are characterized by moderately good substance only in the full open bloom, whereas this new variety has a more substantial substance throughout the life of the flower, from the bud, just beginning to unfold, to the full blown bloom.

(3) The plant of "Charlotte Armstrong" is characterized by an upright spreading habit, whereas this new variety is upright in habit.

(4) The color of the young foliage of this new variety is distinctly bright red, whereas the young foliage of "Charlotte Armstrong" is characterized by a mixture of green and red pigment.

(5) This new variety is not as tall and rangy in habit as the seed parent.

Asexual reproduction of this new variety shows the foregoing characteristics come true to form and are established.

In the accompanying drawing are shown specimens of this new variety with the blooms at different stages of development from bud to full blown flowers and the foliage showing young and mature leaves.

This new variety was asexually reproduced at Ontario, California, by budding.

The following is a detailed description of the new variety, all reference to color being in accordance with the Robert F. Wilson Horticultural Colour Chart (1938), except where indicated to be in accordance with Ridgway's Color Standards and Nomenclature:

Type: Bush; outdoor; seedling; for cut flowers and garden decoration.
Class: Hybrid tea.
Breeding: Seedling.
*Seed parent.*—"Charlotte Armstrong" (Pl. Pat. #455).
*Pollen parent.*—Unnamed seedling.
Propagation: Holds its distinguishing characteristics through succeeding propagations.

*Flower*

Locality where grown: Ontario, California.
Flowers borne: Usually singly, sometimes two or more, to stem; in irregular cluster; on normal strength medium length stems.
Quantity of bloom: Moderate; outdoors.
Continuity: Intermittent during growing season.
Fragrance: Moderate; musk to tea.
Bud:
*Peduncle.*—Average length to long; average caliper to heavy; erect; stiff; smooth except for a few very small gland-tipped cilia. Color—Ocher Red, Plate XXVII (Ridgway), overlying Cosse Green, Plate V (Ridgway).

*Before calyx breaks.*—Size—medium. Form—medium length; pointed; with foliaceous appendages and glandular bloom on the surface of the bud; with much cut foliaceous parts extending beyond the tip of the bud equal to one-half or more of its length.

*As calyx breaks.*—Color—Cardinal Red, Plate 822/1, page 168, with shadings of Chrysanthemum Crimson, Plate 824, page 169.

*Sepals.*—Inner surface—with tomentum; margins exposed have stipitate glands, those that are covered have tomentum.

*As first petal opens.*—Size—average. Form—medium length; ovoid to urn-shaped. Color—outside—Blood Red, Plate 820/2, page 166, overlaid with Currant Red, Plate 821/1, page 167. Basal area is Aureolin, Plate 3/1, page 3; inside—near Blood Red, Plate 820/2, page 166. Basal region is Aureolin, Plate 3, page 3.

*Opening.*—Opens up well. Is not retarded from opening by cold, hot, or dry weather.

Bloom: Size, when fully open—average to large; 3¼ inches to 4¼ inches.

*Petalage.*—Double; from 25 to 40 petals plus 10 to 20 petaloids; arranged regularly.

*Form.*—High centered at first; remaining high centered; petals at first somewhat upright with tips reflexed; tips becoming later at maturity more reflexed outward with outermost petal margins loosely rolled downward.

Petals:

*Texture.*—Medium to thick; with inside slightly velvety and outside satiny.

*Shape.*—Outside—broadly obovate. Intermediate—obovate with apex rounded with one to two notches occasionally. Inside—obovate with apex rounded with usually one to two notches.

*Color.*—Colors may be modified by being overlaid or shaded with other colors.

This description of a newly opened flower was made from a rose grown outdoors in the month of September, at Ontario, California:

*Color.*—*Outside petal*—outside surface: between Cardinal Red, Plate 822/1, page 168, and Chrysanthemum Crimson, Plate 824/2, page 169; inside surface—near Cardinal Red, Plate 822/3, page 168. *Intermediate petal*—outside surface: Cardinal Red, Plate 822/3, page 168; inside surface: between Currant Red, Plate 821/3, page 167, and Cardinal Red, Plate 822/3, page 168. *Inner petal*—outside surface: near Rose Red, Plate 724/1, page 158; inside surface: Cardinal Red, Plate 822, page 168.

This description was made from a rose that was open for three days outdoors in the month of October, at Ontario, California:

*Color.*—*Outside petal*—outside surface: between Cherry, Plate 722/2, page 157, and Cardinal Red, Plate 822/3, page 168; inside surface: Rose Red, Plate 724, page 158, and Rose Red, Plate 724/3, page 158. *Inside petal*—outside surface: between Cherry, Plate 722/2, page 157, and Cardinal Red, Plate 822/3, page 168; inside surface: Rose Red, Plate 724/1, page 158, with shadings of Rose Red, Plate 724, page 158.

*General color effect.*—Newly opened flower—Currant Red, Plate 821/3, page 167. Three days open—Rose Red, Plate 724, page 158.

*Behavior.*—Drop off cleanly except for occasional petaloids; not affected by cold, hot or dry weather.

*Flower longevity.*—On bush in garden—4 days in October. Cut roses grown outdoors kept at living-room temperatures—3 days in October.

*Reproductive organs*

Stamens: Average number; arranged regularly about pistils, a few mixed with petaloids.

Filaments: Medium length to long (7 to 15 mm. long); most with anthers. Color—near Capsicum Red, Plate 715/3, page 92.

Anthers: Medium size; all open at once approximately. Color—upper side—Aureolin, Plate 3/2, page 3; under side—Aureolin, Plate 3/2, page 3, tinged slightly with Rose Madder, Plate 23/3, page 23.

Pollen: Moderate. Color—Aureolin, Plate 3/2, page 3.

Pistils: Average number, approximately 75.

Styles: Moderately even; average length; average caliper; bunched. Color—Bordeaux, Plate XII (Ridgway).

Stigma: Buttercup Yellow, Plate 5/3, page 5, with translucent effect.

Ovaries: Usually most enclosed in calyx.

Hips: None available for description.

Sepals: Permanent; medium length; recurved. Color—inside: Light Grape Green, Plate XLI (Ridgway); outside: near Scheeles Green, Plate 860/2, page 175, lightly shaded near tips and sun exposed portions with Acajou Red, Plate XIII (Ridgway).

Seeds: None available.

*Plant*

Foliage:

*Leaves.*—Compound of usually 3 to 5 leaflets; normally abundant; medium size; moderately soft; glaucous.

*Leaflets.*—Ovate with apex acute; base round to obtuse; margin doubly serrate; margins slightly rolled downward.

*Color.*—*Mature*—upper surface: Dark Dull Yellow-Green, Plate XXXII (Ridgway); under surface: between Light Grape Green, Plate XLI (Ridgway) and Asphodel Green, Plate XLI (Ridgway). *Young*—upper surface: near Burnt Lake, Plate XII (Ridgway); later becoming replaced with Peacock Green, Plate VI (Ridgway); under surface: near Bordeaux, Plate XII (Ridgway), overlaid on more mature leaves with Grass Green, Plate VI (Ridgway).

*Rachis.*—Average size; upper side grooved with some stipitate glands on edges; under side prickly and with stipitate glands.

*Stipules.*—Medium length; medium width with medium length points turning out at an angle of about 45°.

*Disease.*—Slightly more than average resistant to mildew.

Growth:

*Habit.*—Bushy; upright; much branched.

*Growth.*—Free.

*Canes.*—Medium caliper.

*Main stems.*—Color—near Oil Green, Plate V (Ridgway). *Large prickles*—many; medium length; hooked slightly downward; with medium length, medium narrow base. Color—Mikado Brown, Plate XXIX (Ridgway). *Small prickles*—few. Color—Auburn, Plate I (Ridgway). *Hairs*—none.

*Branches.*—Color—near Light Elm Green, Plate XVII (Ridgway). *Large prickles*—many; short to medium length; hooked slightly downward; with short, medium narrow base. Color—Chalcedony Yellow, Plate XVII (Ridgway). *Small prickles*—several. Color—Chalcedony Yellow, Plate XVII (Ridgway). *Hairs*—none.

*New shoots.*—Color—Absinthe Green, Plate XXXI (Ridgway), tinged with Vandyke Red, Plate XIII (Ridgway) on portion exposed to sun. *Large prickles*—several to many; medium length; almost straight, some hooked slightly downward; with short medium narrow base. Color—Amaranth Pink, Plate XII (Ridgway), at base, underlaid and tipped with Uranium Green, Plate 63/2, page 63, to Russet-Vinaceous, Plate XXXIX (Ridgway), progressively with age. *Small prickles*—several. Color—Varies from Pomegranate Purple, Plate XII (Ridgway) to Russet-Vinaceous, Plate XXXIX (Ridgway), progressively with age. *Hairs*—none.

I claim:

A new and distinct variety of rose plant, characterized as to novelty by the bright, unfading red color of its flowers; heavy texture of petals resistant to injury from weather conditions; regularity of both bud and flower form; long lasting quality of flowers on bush or in the cut flower; unusual color of both young and mature leaves; abundance of the foliage, and bushy upright habit of plant growth, substantially as shown and described.

HERBERT C. SWIM.

No references cited.